(12) United States Patent
Ishida (10) Patent No.: US 7,812,222 B2
(45) Date of Patent: Oct. 12, 2010

(54) METHOD OF TRANSDUCING GENE INTO PLANT MATERIAL

(75) Inventor: Yuji Ishida, Iwata (JP)

(73) Assignee: Japan Tobacco Inc., Tokyo (JP)

( * ) Notice: Subject to any disclaimer, the term of this patent is extended or adjusted under 35 U.S.C. 154(b) by 962 days.

(21) Appl. No.: 10/567,866

(22) PCT Filed: Aug. 5, 2004

(86) PCT No.: PCT/JP2004/011237

§ 371 (c)(1),
(2), (4) Date: Sep. 21, 2006

(87) PCT Pub. No.: WO2005/017169

PCT Pub. Date: Feb. 24, 2005

(65) Prior Publication Data

US 2007/0136898 A1    Jun. 14, 2007

(30) Foreign Application Priority Data

Aug. 13, 2003    (JP) .............................. 2003-293125

(51) Int. Cl.
*C12N 15/84*    (2006.01)
*C12N 15/82*    (2006.01)

(52) U.S. Cl. ................. 800/294; 800/317.3; 800/320.1; 800/320.2; 435/424; 435/425; 435/430.1; 435/469

(58) Field of Classification Search ........................ None
See application file for complete search history.

(56) References Cited

U.S. PATENT DOCUMENTS

| 5,591,616 | A | 1/1997 | Hiei et al. |
| 6,329,571 | B1 | 12/2001 | Hiei |
| 6,384,301 | B1 | 5/2002 | Martinell et al. |
| 6,492,174 | B1 | 12/2002 | Pullman et al. |
| 2002/0157139 | A1 | 10/2002 | Martinell et al. |

FOREIGN PATENT DOCUMENTS

| EP | 486233 | * | 5/1992 |
| EP | 0 604 662 A1 | | 7/1994 |
| EP | 0 672 752 A1 | | 9/1995 |
| EP | 1 306 440 A1 | | 5/2003 |
| EP | 1 306 441 A1 | | 5/2003 |
| EP | 1 437 409 A1 | | 7/2004 |
| JP | 2000-342253 A | | 12/2000 |
| JP | 2000-342255 A | | 12/2000 |
| JP | 2000-342256 A | | 12/2000 |
| WO | WO-95/06722 A1 | | 3/1995 |
| WO | WO-99/48355 A1 | | 9/1999 |
| WO | WO-02/12520 A1 | | 2/2002 |
| WO | WO-03/027290 A1 | | 4/2003 |

OTHER PUBLICATIONS

Knittel et al. Plant Cell Reports 14: 81-86 (1994).*
Cheng et al. Plant Cell Reports 16: 127-132 (1996).*
Finer et al. Plant Cell Reports 11: 323-328 (1992).*
Amoah et al., Journal of Experimental Botany, vol. 52, No. 358, May 2001, pp. 1135-1142.
Chan et al., Plant Molecular Biology, vol. 22, 1993, pp. 491-506.
Hiei et al., The Plant Journal, vol. 6, No. 2, 1994, pp. 271-282.
Hoekema et al., Nature, vol. 303, May 12, 1983, pp. 179-180.
Ishida et al., Nature Biotechnology, vol. 14, Jun. 1996, pp. 745-750.
Komari, Theoretical and Applied Genetics, vol. 80, 1990, pp. 167-171.
Komari et al., Molecular Improvements of Cereal Crops, 1999, pp. 43-82.
Lindsey et al., Plant Tissue Culture Manual, B7, 1991, pp. 1-13.
McCormick, Plant Tissue Culture Manual, B6, 1991, pp. 1-9.
Potrykus et al., Genetic Engineering of Crop Plants, 1998, pp. 119-159.
Rogers et al., Methods for Plant Molecular Biology, 1988, pp. 423-436.
Tingay et al., The Plant Journal, vol. 11, No. 6, 1997, pp. 1369-1376.
Trick et al., Transgenic Research, vol. 6, 1997, pp. 329-336.
Visser, Plant Tissue Culture Manual, B5, 1991, pp. 1-9.
Weber et al., Plant Cell Reports, vol. 21, 2003, pp. 475-482.

* cited by examiner

*Primary Examiner*—David T Fox
(74) *Attorney, Agent, or Firm*—Birch, Stewart, Kolasch & Birch, LLP (57) ABSTRACT

The present invention relates to a method of introducing a gene into plant material via *Agrobacterium*. A method of the present invention is characterized in that it comprises: 1) pressurizing a plant material, and then 2) infecting the plant material with an *Agrobacterium*.

15 Claims, 3 Drawing Sheets

METHOD OF TRANSDUCING GENE INTO PLANT MATERIAL

TECHNICAL FIELD

The present application is a national stage filing under 35 U.S.C. §371 of international application number PCT/JP2004/011237 filed Aug. 5, 2004, which claims the benefit of priority of Japanese Patent Application No. 2003-293125, filed on Aug. 13, 2003.

The present invention relates to method of introducing gene into plant material via *Agrobacterium*.

BACKGROUND ART

*Agrobacterium*-mediated gene transduction is a method for transforming plants through the use of a function of *Agrobacterium*. A soil bacterium *Agrobacterium tumefaciens* functions in such a manner that the T-DNA which forms a part of its Ti (tumor-inducing) plasmid involved in the pathogenicity of the *Agrobacterium*, is integrated into the genome of a plant when it infects the plant. *Agrobacterium*-mediated plant transformation is a method of introducing a desired gene into the genome of a plant through the use of the function of *Agrobacterium* described above by constructing a transforming plasmid in which the T-DNA region of the Ti plasmid is replaced by the gene desired to be introduced into the plant genome, and using *Agrobacterium* prepared to carry the transforming plasmid in place of the Ti plasmid.

*Agrobacterium*-mediated plant transformation was originally developed mainly as a method for transforming dicotyledons because *Agrobacterium* were thought to infect only dicotyledons but not monocotyledons. Various attempts for *Agrobacterium*-mediated gene transduction into monocotyledons were also made, and super-binary vectors having a part of the virulent genes of super-virulent *Agrobacterium* strains were developed and reported to be useful for stably transforming even monocotyledons such as rice and maize with relatively high efficiency (Hiei, et al., 1994; Ishida, et al., 1996; Japanese Patent No. 2,649,287; Japanese Patent No. 3,329,819). Successful examples of *Agrobacterium*-mediated transformation of monocotyledons such as wheat, barley and sorghum were also reported, and *Agrobacterium*-mediated transformation also became to be widely applied to monocotyledons.

*Agrobacterium*-mediated transformation generally has many advantageous features such as high efficiency, low copy number transgenes, transferability of such a specific region as T-DNA without being fragmented, and short-term culture for obtaining transformants resulting in little somaclonal variations. Thus, it is widely used as the most useful means for transforming many plant species irrespective of whether they are dicotyledonous or monocotyledonous.

*Agrobacterium*-mediated transformation is equally performed in all plants by contacting a material tissue with an *Agrobacterium* suspension, coculturing them and then selecting a transformed cell to produce a transformed plant, though the materials and the compositions of the culture media vary with plant species. Typically, the plant tissue used as a material is infected with *Agrobacterium* without any special treatment except for optional sterilization (Rogers et al. 1988, Visser 1991, McCormick 1991, Lindsey et al. 1991).

*Agrobacterium*-mediated transformation has been reported for many plant species, but has the disadvantage that the transformation efficiency widely varies with plant species, genotypes and material tissues (Potrykus et al. 1998). It is important to develop a technology enabling transformed plants to be stably obtained with high efficiency throughout the year because many transformed plants must be produced when a variety containing a practical gene is to be cultured. Moreover, transformation methods independent from plant species and genotypes would be very useful for efficiently culturing practical varieties. Additionally, transformation methods independent from plant tissues used as materials would be required for efficient transformation.

As described above, it is important to develop a method capable of improving gene transduction efficiency or transforming plant species or genotypes involving difficulty in gene transduction, and many reports have already existed. However, many of them focus on the modification of the compositions of culture media, marker genes or promoters or the investigation of materials. Some reports discussed methods for treating plant tissues before infection with *Agrobacterium* to adapt them for gene transduction, but all of them contemplated improving infection efficiency by injuring tissues via incision (Chan et al. 1993), particle gun (Tingay et al. 1997), sonication (Trick and Finer 1997, Amoah et al. 2001), enzyme treatment (Weber et al. 2003), etc.

Hiei et al. found that plant tissues are transformed with higher efficiency by *Agrobacterium*-mediated gene transduction after centrifugation as compared with untreated tissues (WO 02/12520, Japanese Patent Laid-Open Publication No. 2000-342256). Although the details of the mechanism via which transformation efficiency is improved by centrifugation are unknown, it is thought that cells turned into a physiological state suitable for gene transduction by centrifugation unlike the methods of physically injuring tissues as described above. It was also found that tissues having undergone heat treatment or both of centrifugation and heat treatment are transformed with higher efficiency as compared with untreated tissues (Japanese Patent Laid-Open Publication No. 2000-342255, Japanese Patent Laid-Open Publication No. 2000-342253).

Teasdale et al. filed a patent application for a method of transformation comprising immersing a plant tissue in a medium including an infective transformation vector and reducing and/or raising the pressure (WO 99/48335). Teasdale et al. describe that the over pressure is designed to promote infiltration of the transformation vector into the plant tissue. However, they describe only an experimental example of a treatment under negative pressure, but no example of treatment under positive pressure. Thus, no data is shown to support that pressurization is effective for improving gene transduction efficiency.

Pullman and Peter filed a patent application for a method of improving the frequency of embryogenic callus formation by culturing a plant tissue under pressure (U.S. Pat. No. 6,492, 174). They describe that culturing at 1.5 atm gave the highest frequency of callus formation in the experiment at pressures of 1-2.5 atm for the culture period of 8 weeks. All the other experiments were performed at a very low positive pressure such as 1.5 atm. There is no description about the effect of pressurization on gene transduction.

Patent Publication No. 1: International Publication No. WO 02/12520.
Patent Publication No. 2: International Publication No. WO 99/48355.
Patent Publication No. 3: U.S. Pat. No. 6,492,174.
Patent Publication No. 4: Japanese Patent No. 2,649,287.
Patent Publication No. 5: Japanese Patent No. 3,329,819.
Patent Publication No. 6: Japanese Patent Laid-open Publication No. 2000-342256.
Patent Publication No. 7: Japanese Patent Laid-open Publication No. 2000-342255.

Patent Publication No. 8: Japanese Patent Laid-open Publication No. 2000-342253.

Patent Publication No. 9: International Publication No. WO 95/06722.

Patent Publication No. 10: International Publication No. WO 03/027290.

Non-Patent Publication No. 1: Amoah, B. K., Wu, H., Sparks, C. and Jones, H. D. (2001) Factors influencing *Agrobacterium*-mediated transient expression of uidA in wheat inflorescence tissue. Journal of Experimental Botany 52: 1135-1142.

Non-Patent Publication No. 2: Chan, M-T., Cheng, H-H., Ho, S-L., Tong, W-F. and Yu, S-M. (1993) *Agrobacterium*-mediated production of transgenic rice plants expressing a chimeric a-amylase promoter/β-glucuronidase gene. Plant Molecular Biology, 22, 491-506.

Non-Patent Publication No. 3: Hiei, Y., Ohta, S., Komari, T. and Kumashiro, T. (1994) Efficient transformation of rice (*Oryza sativa* L.) mediated by *Agrobacterium* and sequence analysis of the boundaries of the T-DNA. The Plant Journal, 6, 271-282.

Non-Patent Publication No. 4: Hoekema, A., Hirsch, P. R., Hooykaas, P. J. J. and Schilperoort, R. A. (1983) A binary plant vector strategy based on separation of vir- and T-region of the *Agrobacterium tumefaciens* Ti-plasmid. Nature, 303, 179-180.

Non-Patent Publication No. 5: Ishida, Y., Saito, H., Ohta, S., Hiei, Y., Komari, T. and Kumashiro, T. (1996) High efficiency transformation of maize (*Zea mays* L.) mediated by *Agrobacterium tumefaciens*. Nature Biotech. 14: 745-750.

Non-Patent Publication No. 6: Komari, T. (1990) Genetic characterization of a double-flowered tobacco plant obtained in a transformation experiment. Theor. Appl. Genet. 80: 167-171.

Non-Patent Publication No. 7: Komari, T. and Kubo, T. (1999) Methods of Genetic Transformation: *Agrobacterium tumefaciens*. In Vasil, I. K. (ed.) Molecular improvement of cereal crops. Kluwer Academic Publishers, Dordrecht, pp. 43-82.

Non-Patent Publication No. 8: Lindsey, K., Gallois, P. and Eady, C. (1991) Regeneration and transformation of sugarbeet by *Agrobacterium tumefaciens*. Plant Tissue Culture Manual B7: 1-13. Kluwer Academic Publishers.

Non-Patent Publication No. 9: McCormick, S. (1991) Transformation of tomato with *Agrobacterium tumefaciens*. Plant Tissue Culture Manual B6: 1-9. Kluwer Academic Publishers.

Non-Patent Publication No. 10: Potrykus, I., Bilang, R., Futterer, J., Sautter, C. and Schrott, M. (1998) Agricultural Biotechnology, NY: Mercel Dekker Inc. pp. 119-159.

Non-Patent Publication No. 11: Rogers, S. G., Horsch, R. B. and Fraley, R. T. (1988) Gene transfer in plants: Production of transformed plants using Ti plasmid vectors. Method for Plant Molecular Biology, CA: Academic Press Inc. pp. 423-436.

Non-Patent Publication No. 12: Tingay, S., McElroy, D., Kalla, R., Fieg, S., Wang, M., Thornton, S. and Brettell, R. (1997) *Agrobacterium tumefaciens*-mediated barley transformation. The Plant Journal 11: 1369-1376.

Non-Patent Publication No. 13: Trick, H. N. and Finer, J. J. (1997) SAAT: sonication-assisted *Agrobacterium*-mediated transformation. Transgenic Research 6: 329-336.

Non-Patent Publication No. 14: Visser, R. G. F. (1991) Regeneration and transformation of potato by *Agrobacterium tumefaciens*. Plant Tissue Culture Manual B5: 1-9. Kluwer Academic Publishers.

Non-Patent Publication No. 15: Weber, S., Friedt, W., Landes, N., Molinier, J., Himber, C., Rousselin, P., Hahne, G. and Horn, R. (2003) Improved *Agrobacterium*-mediated transformation of sunflower (*Helianthus annuus* L.): assessment of macerating enzymes and sonication. Plant Cell Reports 21: 475-482.

DISCLOSURE OF THE INVENTION

Problems to be Solved by the Invention

The present invention provides a method of transducing gene into plant material via *Agrobacterium*. The method of the present invention is characterized in that it comprises:
1) pressurizing the plant material, and then
2) infecting the plant material with an *Agrobacterium*.

The method of the present invention improves gene transduction efficiency as compared with cases wherein the step 1) of pressurization is not conducted.

Means for Solving the Problems

As a result of careful studies to solve the problems described above, we found that stable and highly efficient gene transduction is achieved by coculturing plant tissues with *Agrobacterium* after pressurizing the plant tissues as compared with untreated tissues. We also ascertained that the effect of pressurization on improving gene transduction efficiency is found irrespective of whether the plant is dicotyledonous or monocotyledonous. When transformed cells were selected from the transfected plant materials and the transformed plants were re-differentiated, we found that pressurized materials dramatically improved in transformation efficiency over untreated materials. Moreover, we demonstrated that the growth of plant tissues (e.g., callus growth from immature embryos) is enhanced by pressurization.

Accordingly, the present invention relates to a method of introducing gene into plant material via *Agrobacterium*, comprising:
1) pressurizing the plant material, and then
2) infecting the plant material with an *Agrobacterium*.

That is, pressurization of the plant material herein is performed before but not simultaneously with infection with *Agrobacterium*.

Pressurization is preferably performed in the range of, but not limited to, 1.7 atm to 10 atm, more preferably 2.4 atm to 8 atm, most preferably 4 atm to 8 atm. The pressure ranges shown above are on the basis of normal pressure defined as 1 atm. Thus, pressurization at e.g. 1.7 atm means a condition at normal pressure plus 0.7 atm, and pressurization at 10 atm means a condition at normal pressure plus 9 atm. The pressurization period is not limited, but preferably 0.1 seconds to 4 hours, more preferably 1 second to 30 minutes.

Pressurization may be performed in a liquid or gas. Liquids that can be used include, but not limited to, water (e.g., sterilized distilled water), liquid media and other liquids not inhibiting the growth of plant tissues. Gases that can be used include, but not limited to, air, oxygen and other gases not inhibiting the growth of plant tissues.

Pressurization procedures can be performed by e.g., combining syringes, holding the syringes by a clamp and tightening the clamp to increase the pressure in the syringes. The pressurization force can be calculated from e.g., the loss of the volume of air in the syringes. Alternatively, pressurization may also be performed by 1) supplying a gas into a vessel containing a plant tissue from a compressor or the like to increase the inner pressure of the vessel, or 2) submerging a plant tissue contained in a bag or the like sealed against the outside air in a liquid to hydraulically pressurize it.

The method of the present invention is characterized by using pressurized plant materials to be infected with an *Agrobacterium*, and well-known methods for *Agrobacterium*-mediated gene transduction or transformation per se can be applied.

Methods for *Agrobacterium*-Mediated Gene Transduction and Transformation

*Agrobacterium*-mediated gene transduction typically comprises the steps of:

a) preparing a plant material;

b) preparing an *Agrobacterium* carrying a vector containing a desired transgene; and c) infecting the plant material prepared in step a) with the *Agrobacterium* prepared in step b).

In order to obtain a transformant, the step c) may be further followed by the steps of:

d) selecting a transformed cell; and e) optionally regenerating the selected transformant.

Step a)

The "plants" used herein for gene transduction include both monocotyledons and dicotyledons. Monocotyledons include, but not limited to, rice, maize, barley, wheat, asparagus, sorghum and the like, preferably rice or maize. Dicotyledons include, but not limited to, tobacco, soybean, potato, sunflower and the like, preferably tobacco.

The "plant materials" encompass all the aspects of plants to be used for *Agrobacterium*-mediated transformation of plants including, but not limited to, cells of the plants; plant tissues, immature embryos, calli or adventitious embryo-like tissues (hereinafter referred to as calli or the like, or simply calli) of leaves, roots, stems, fruits or any other organs; or the whole plants.

Desirable forms of plants used in the methods of the present invention are immature embryos or calli, most desirably immature embryos. As used herein, the expressions plant cell, tissue and whole plant have the same meanings as commonly used in the art. As used herein, the immature embryo means the embryo of an immature seed under maturation after pollination. The stage (maturation phase) of the immature embryo used in the methods of the present invention is not specifically limited, but it may be collected at any stage after pollination. However, it is preferably at a stage of two days or more after pollination. Preferably, the embryonic disc of an immature embryo capable of inducing a callus having the ability to regenerate a normal individual after transformation is used. The immature embryo is preferably an immature embryo of an inbred line, F1 between inbred lines, F1 between an inbred line and an open-pollinated variety, or a commercially available F1 variety. As used herein, the callus means an undifferentiated cell clump under uncontrolled growth. The callus can be obtained by culturing a differentiated cell of a plant tissue in a medium containing a plant growth regulator such as auxin (e.g., 2,4-D (2,4-dichlorophenoxyacetic acid)) or cytokinin (referred to as dedifferentiation medium). The treatment for obtaining a callus is called dedifferentiation treatment and this process is called dedifferentiation process.

In step a), an optimal material for transformation is prepared by extracting a plant tissue, immature embryo or the like as appropriate from a plant, seed or the like. Optionally, the plant material may be cultured before it is infected with an *Agrobacterium*.

The present invention is characterized in that the plant material is pressurized during the process of preparing the plant material in step a), or before it is infected with an *Agrobacterium* in step c) after preparation.

Step b)

A soil bacterium *Agrobacterium* (*Agrobacterium tumefaciens*) has long been known to induce crown gall disease in many dicotyledons, and in 1970s, it was discovered that its Ti plasmid is involved in pathogenicity and that the T-DNA forming a part of the Ti plasmid is integrated into plant genomes. Subsequently, it was shown that the T-DNA contains genes involved in the synthesis of hormones necessary for inducing cancers (cytokinin and auxin) and that these genes are expressed in plants though they are bacterial genes. Excision of the T-DNA and its transduction to plants require genes existing in the virulence region (vir region) on the Ti plasmid, and excision of the T-DNA requires border sequences flanking the T-DNA. Another *Agrobacterium*, *Agrobacterium rhizogenes* has a similar system based on its Ri plasmid (e.g., Japanese Patent Laid-Open Publication No. 2000-342256, FIGS. 3 and 4).

A desired gene was expected to be integrated into plant genomes when it is inserted onto the T-DNA because the T-DNA is integrated into plant genomes by infection with *Agrobacterium*. However, it was difficult to insert a gene onto the T-DNA on the Ti plasmid by standard genetic engineering techniques because the Ti plasmid is as large as 190 kb or more. Thus, a method for inserting an exogenous gene onto the T-DNA was developed.

Initially, disarmed strains in which the hormone-synthesizing genes have been removed from the T-DNA of the tumor-inducing Ti plasmid such as LBA4404 (Hoekema et al., 1983), C58C1 (pGV3850), and GV3TillSE were prepared. Two methods were developed for introducing a desired gene into the T-DNA of the Ti plasmid of *Agrobacterium* or introducing the T-DNA carrying a desired gene into *Agrobacterium* using these strains. The first method is called as the intermediate vector method wherein an intermediate vector that is easy to genetically manipulate enough to insert a desired gene in it and that can be replicated in *E. coli* is inserted into the T-DNA region of a disarmed Ti plasmid of *Agrobacterium* by homologous recombination via triparental mating.

The second method is called as the binary vector method based on the finding that the vir region is required for integration of the T-DNA into plants but need not be present on the same plasmid to serve its functions. There exist virA, virB, virC, virD, virE and virG in the vir region (Dictionary of Plant Biotechnology, published by Enterprise (1989)), and the vir region refers to a region containing all of these virA, virB, virC, virD, virE and virG. Thus, a binary vector carrying the T-DNA integrated into a small plasmid replicable in both *Agrobacterium* and *E. coli* is introduced into *Agrobacterium* having a disarmed Ti plasmid, and used.

Transduction of a binary vector into *Agrobacterium* can be performed by known methods such as electroporation and triparental mating. Binary vectors include pBIN19, pBI121, pGA482, etc., and many novel binary vectors based on them were constructed and used for transformation. In the Ri plasmid system, similar vectors were constructed and used for transformation.

*Agrobacterium* A281 is a super-virulent strain that has a wide host range and higher transformation efficiency than those of other strains. This characteristic is attributed to pTiBo542 of the Ti plasmid carried by A281. Two novel systems were developed using pTiBo542 until now. One uses EHA101 and EHA105 strains carrying a disarmed Ti plasmid of pTiBo542 and serves for transformation of various plants as a system having a high transforming ability by applying these strains to the binary vector system described above.

The other is a 'super-binary' vector (Hiei et al. (1994); Ishida et al. (1996); Komari et al. (1999); WO95/06722) system (e.g., FIG. 4 of Japanese Patent Laid-Open Publication No. 2000-342256). This system is a kind of binary vector system because it consists of a disarmed Ti plasmid having the vir region (virA, virB, virC, virD, virE and virG (hereinafter sometimes referred to as "vir fragment regions")) and a plasmid having the T-DNA. However, it differs in that it uses a super-binary vector containing a fragment of the vir region substantially free from at least one of the vir fragment regions (preferably a fragment including at least virB or virG, more preferably a fragment including virB and virG) in the plasmid having the T-DNA, i.e. a binary vector. Homologous recombination via a three-line crossing method can be used as a convenient method for introducing the T-DNA region containing a desired gene into *Agrobacterium* carrying a super-binary vector.

*Agrobacterium* that can be used as hosts in the methods of the present invention are not specifically limited, but preferably include *Agrobacterium tumefaciens* (e.g., *Agrobacterium tumefaciens* LBA4404 (Hoekema et al., 1983) and EHA101 as described above).

According to the methods of the present invention, significant effects can be obtained by using any gene transduction system based on the expression of the genes in the virulence (vir) region in *Agrobacterium*. Thus, any vector system can be used such as intermediate vectors, binary vectors, super-virulent binary vectors and super-binary vectors as described above to benefit from the present invention. The same effects can also be obtained by using different vector systems obtained by modifying these vectors (e.g., by excising a part or all of the vir region of *Agrobacterium* and additionally integrating it into a plasmid, or excising a part or all of the vir region and introducing it into *Agrobacterium* as a part of a novel plasmid). According to the methods of the present invention, the infection efficiency can also be virtually improved with wild-type *Agrobacterium* by increasing the transduction efficiency of the wild-type T-DNA region into plants.

A desired gene to be introduced into plants can be inserted between restriction endonuclease sites in the T-DNA region of the plasmid described above according to standard procedures, and can be selected on the basis of a suitable selective marker such as a gene having resistance to drugs such as kanamycin and paromomycin simultaneously or separately inserted into the plasmid. A desired DNA may not be readily introduced into the T-DNA region of a large plasmid having many restriction endonuclease sites by conventional subcloning methods. In such cases, the desired DNA can be transfected by homologous recombination in cells of *Agrobacterium* via triparental mating. The size of the transgene is not limited, but preferably about 100 bp to 200 kbp.

Transduction of the plasmid into an *Agrobacterium* such as *Agrobacterium tumefaciens* can be accomplished by conventional methods such as triparental mating as described above, electroporation, electroinjection, and chemical treatments with PEG or the like.

The gene to be introduced into plants is basically located between the border sequences flanking the T-DNA similarly to conventional techniques. However, only one border sequence may exist because the plasmid is circular, or three or more border sequences may exist when multiple genes are to be located at different sites. The gene may also be located on the Ti or Ri plasmid or on another plasmid in *Agrobacterium*. Alternatively, it may also be located on multiple types of plasmids.

Step c)

*Agrobacterium*-mediated gene transduction can be performed simply by contacting a plant material with an *Agrobacterium*. For example, it can be performed by preparing an *Agrobacterium* suspension having a cell density of about $10^6$ to $10^{11}$ cells/ml, immersing a plant material in this suspension for 3 to 10 minutes, and then coculturing them on a solid medium for several days.

Preferably, the plant material is cocultured with *Agrobacterium* at the same time as the plant material is infected with *Agrobacterium* or before *Agrobacterium* is removed after infection. Known media can be used as culture media. For example, nN6-As medium, nNB-As medium and LS-AS medium as used in the examples below or other media such as N6S3-AS medium and 2N6-AS medium (Hiei et al. 1994) are known.

In the present invention, the plant material may be subjected to at least one treatment selected from the group consisting of heat treatment, centrifugation and sonication before or during the step c) of infecting the plant material with an *Agrobacterium*. These treatments are also known to increase gene transduction efficiency in *Agrobacterium*-mediated gene transduction into plant materials. For example, centrifugation is described in e.g., WO 02/12520, Japanese Patent Laid-Open Publication No. 2000-342256, and preferably performed at 100 G to 250,000 G for 1 second to 4 hours. Heat treatment is described in e.g., Japanese Patent Laid-Open Publication No. 2000-342255, and preferably performed in a temperature range of 33° C. to 60° C. for 5 seconds to 24 hours. Sonication is described in e.g., Trick and Finer 1997, Amoah et al. 2001.

Any one of these treatments such as pressurization, heat treatment and centrifugation may be performed or combinations of treatments may be performed. For example, Japanese Patent Laid-Open Publication No. 2000-342253 describes combination of heat treatment and centrifugation.

Steps d) and e)

In order to obtain a transformant if desired, the step c) described above should be followed by the steps of:

d) selecting a transformed cell; and e) optionally regenerating the selected transformant.

That is, in order to transform a plant, it is typically necessary to select a plant cell containing an exogenous gene stably integrated into the chromosome after the exogenous gene is transfected into the plant cell.

The step of selecting a transformed cell means selecting a cell having a desired trait based on at least one, preferably both of phenotype data and physical data.

Phenotype data such as transformation efficiency can be obtained by evaluating the expression of a marker gene and/or a selective marker gene cotransfected with a gene desired to be introduced into a plant. Marker genes and/or selective marker genes that can be used include e.g., the GUS (β-glucuronidase) gene, antibiotic-resistant genes (e.g., PPT (phosphinothricin)-resistant genes, kanamycin-resistant genes), etc. When the GUS gene is used as a marker gene, transformation efficiency can be evaluated from coloration due to the cleavage of X-gulc (5-bromo-4-chloro-3-indolyl-β-D-glucuronic acid) by GUS. When a gene resistant to an antibiotic is used as a selective marker gene, evaluation can be made from the extent of growth on a selective medium containing the antibiotic after transformation.

To ascertain that the exogenous gene has been stably integrated into the chromosome, it is preferable to obtain physical data such as southern blotting. More preferably, the selecting step may be performed based on transmission to progeny via sexual reproduction and genetic and molecular analyses in progeny populations.

Optionally, the selected transformant may be redifferentiated and the redifferentiated individual may be grown to give a whole plant. Regeneration from the selected transformed cell to a whole plant can be performed by known methods (e.g., Hiei et al. 1994, Ishida et al. 1996).

The methods of the present invention improve gene transduction efficiency and/or transformation efficiency as compared with cases wherein pressurization is not conducted. The gene transduction efficiency can be evaluated by e.g., assessing the range of transient expression of the transgene. In the examples below, the transient expression of the GUS gene in the embryonic discs of immature embryos was evaluated on a scale of five ratings from 1 (occasional spot expression) to 5 (expression on the whole surface of the embryonic disc). Alternatively, it can also be evaluated by counting the total number of spots in cases where the total expression level is low.

The transformation efficiency was calculated by e.g., counting the number of the regenerated plants expressing the GUS gene as transformants among those obtained from inoculated immature embryos and dividing the total number by the number of inoculated immature embryos. Alternatively, it can also be calculated by counting the number of the regenerated plants showing resistance against a selective pressure as transformants and dividing the total number by the number of inoculated immature embryos.

The present invention also provides a method of producing a transformed plant. The method of the present invention comprises:
1) pressurizing a plant material,
2) infecting the plant material with an *Agrobacterium*,
3) selecting a transformed cell, and
4) optionally regenerating the selected transformant.

EFFECTS

The present invention develops inexpensive and convenient gene transduction methods with higher efficiency than conventional *Agrobacterium*-mediated methods. It also provides methods that can be adapted to plant species and varieties involving difficulty in gene transduction by conventional *Agrobacterium*-mediated methods. The methods of the present invention improve gene transduction efficiency and/or transformation efficiency as compared with cases wherein pressurization is not conducted.

Figure 1:
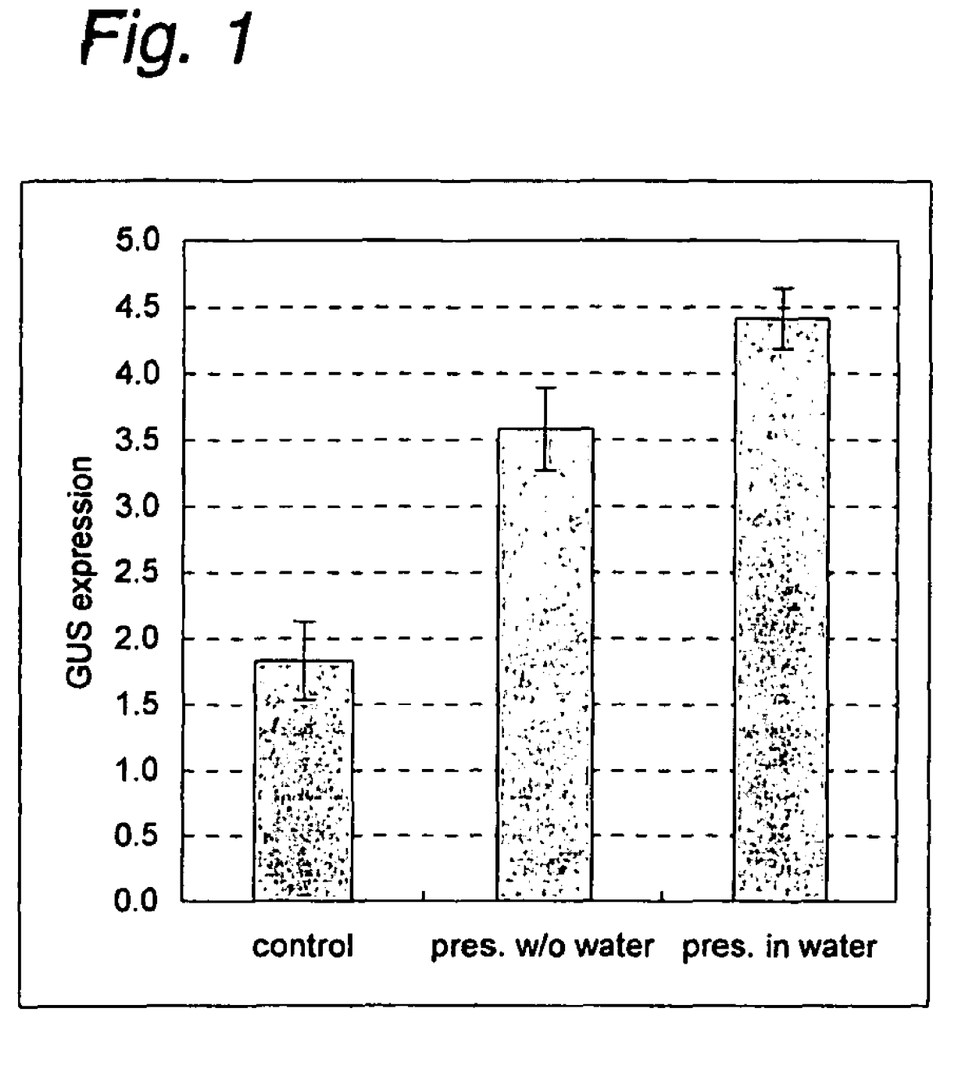
FIG. 1 shows effects of pressurization in a gas on gene transduction efficiency (in rice, variety: Yukihikari).
control: without pretreatment,
pres. w/o water: pressurization at +5.7 atm in a gas for 5 minutes,
pres. in water: pressurization at +6.6 atm in distilled water for 5 minutes.
Figure 3:
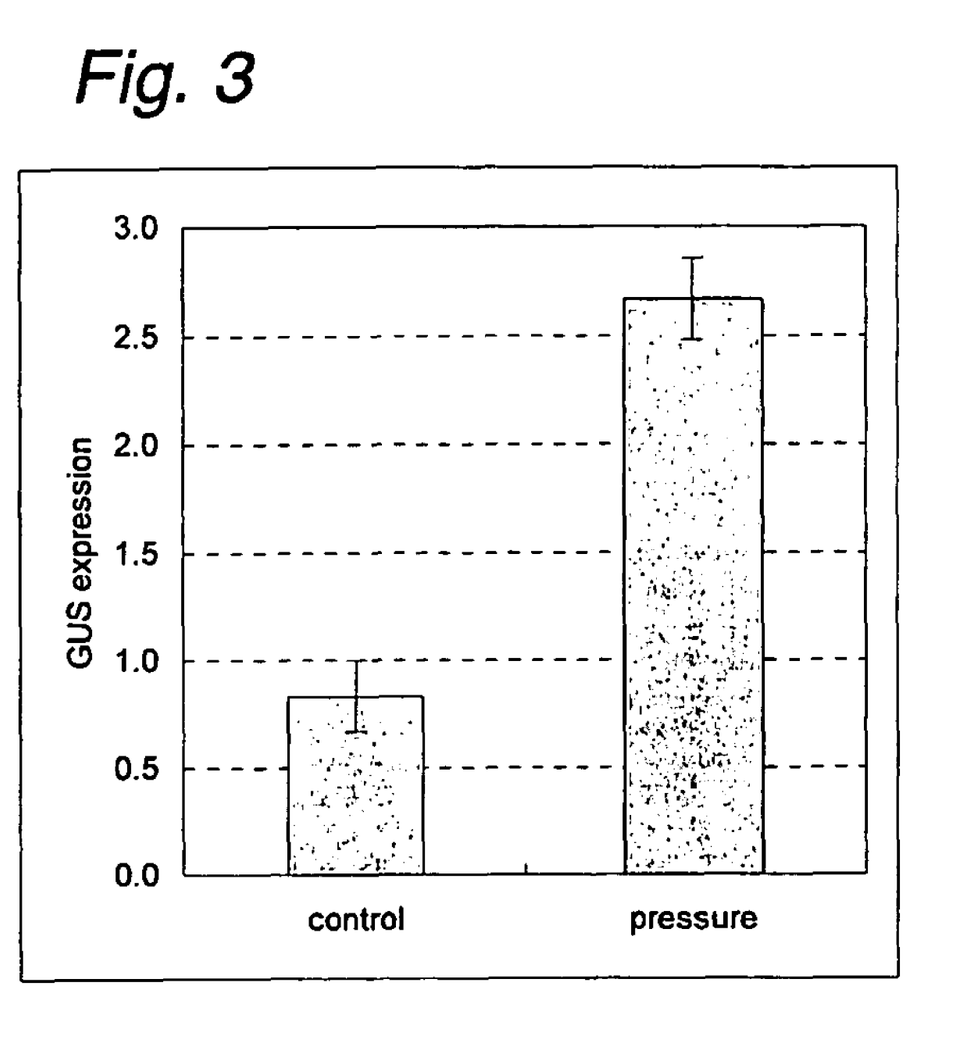
FIG. 3 shows effects of pressurization on gene transduction efficiency (in tobacco, variety: Petit Havana SR1).
control: without pretreatment,
pressure: pressurization at +6.6 atm for 5 minutes.

As shown in FIG. 1, the gene transduction efficiency in a monocotyledon rice was improved by pressurization 2-fold to 3-fold higher than untreated control. As shown in FIG. 3, the gene transduction efficiency in a dicotyledon tobacco was improved by pressurization 3-fold to 4-fold higher than untreated control. Thus, gene transduction efficiency is preferably substantially improved, more preferably 2-fold higher or more by using the methods of the present invention. In addition, the transformation efficiency in rice increased by pressurization 3-fold to 9-fold higher than untreated samples, as shown in Table 1. Thus, transformation efficiency is preferably substantially improved, more preferably 3-fold higher or more by using the methods of the present invention.

BRIEF DESCRIPTION OF THE DRAWINGS

After each treatment, the material was inoculated with LBA4404 (pSB134) and cocultured for 7 days, and then assayed for GUS.

After each treatment, the material was inoculated with LBA4404 (pSB131) and cocultured for 3 days, and then assayed for GUS.

After each treatment, the material was inoculated with LBA4404 (pSB134) and cocultured for 4 days, and then assayed for GUS.

EXAMPLES

The following examples further illustrate the present invention but are not intended to limit the technical scope of the invention. Those skilled in the art can readily add modifications/changes to the present invention on the basis of the description herein, and such modifications/changes are included in the technical scope of the present invention.

Example 1

Effects of Pressurization on Rice Transformation (1) Pressurization
A flame-polished blunt-ended micropipette tip was inserted into the tip end of each of 5-ml disposable syringes and cut off at an appropriate length, and then the end was covered with Parafilm. Aseptically collected immature embryos (varieties: Koshihikari and Asanohikari) were placed in a syringe containing 3 ml of a liquid medium for suspending *Agrobacterium* (AA majorsalts, LS minorsalts, MS vitamins, AA amino acids, 0.2 g/l casamino acids, 4 g/l sucrose, 2 g/l glucose, pH 5.2) or sterilized distilled water. Collected immature embryos (variety: Yukihikari) were placed in a syringe containing no liquid such as culture medium or distilled water. The syringes were combined and held by a clamp, which was tightened to increase the pressure inside the syringes. The syringes were allowed to stand at room temperature under pressure. The pressurization force was calculated from the loss of the volume of air in the syringes. As a control, approximately the same number of immature embryos were collected in a 2-ml Eppendorf tube containing the liquid medium or sterilized distilled water and allowed to stand at room temperature.

(2) Inoculation
The *Agrobacterium* strain and *Agrobacterium* plasmid vector used was an *Agrobacterium tumefaciens* super-binary vector designated LBA4404 (pSB134) (containing the HPT gene linked to a ubiquitin intron driven by a maize ubiquitin promoter and the GUS gene linked to a castor bean catalase intron driven by the Cauliflower Mosaic Virus 35S promoter in the T-DNA region). Construction of pSB134 was performed by inserting a 35S-intron GUS-nos fragment derived from pSB32 as an expression marker into HindIII of pKY205 (Komori et al. WO03/027290).

The syringes were removed from the clamp and the immature embryos in the syringes were transferred to 2-ml Eppendorf tubes containing the liquid medium. LBA4404 (pSB134)

was cultured on AB medium containing 50 mg/l hygromycin and 50 mg/l spectinomycin for 3 to 4 days and scraped with a platinum loop and suspended at a concentration of about $10^9$ cfu/ml in 1 ml of the liquid medium containing 100 μM acetosyringone. The liquid medium was removed from each Eppendorf tube, to which was added 1 ml of a suspension of *Agrobacterium*, and the tube was agitated for 30 seconds in a vortex mixer and then allowed to stand at room temperature for 5 minutes. The immature embryos were plated on nN6-As medium (N6salts, N6 vitamins, 0.5 g/l casamino acids, 0.5 g/l L-proline, 1 mg/l 2,4-D, 0.5 mg/l NAA, 0.1 mg/l 6BA, 20 g/l sucrose, 10 g/l glucose, 10 μM $AgNO_3$, 100 μM acetosyringone, 8 g/l agarose, pH 5.2) or nNB-As medium (N6 majorsalts, B5 minorsalts, B5 vitamins, 0.5 g/l casamino acids, 0.5 g/l L-proline, 2 mg/l 2,4-D, 1 mg/l NAA, 1 mg/l 6BA, 20 g/l sucrose, 10 g/l glucose, 100 μM acetosyringone, 8 g/l agarose, pH 5.2) and cultured in darkness at 25° C. for one week.

(3) Selection and Regeneration

Cocultured immature embryos were divided with a scalpel into 4 to 6 portions, and plated on nN6CC medium (N6salts, N6 vitamins, 0.5 g/l casamino acids, 0.5 g/l L-proline, 1 mg/l 2,4-D, 0.5 mg/l NAA, 0.1 mg/l 6BA, 20 g/l sucrose, 55 g/l sorbitol, 250 mg/l cefotaxime, 250 mg/l carbenicillin, 5 g/l Gelrite, pH 5.8) or NBK4CC (NBK4 majorsalts, B5 minorsalts, B5 vitamins, AA amino acids, 0.5 g/l casamino acids, 0.5 g/l L-proline, 1 mg/l 2,4-D, 0.5 mg/l NAA, 0.1 mg/l 6BA, 20 g/l maltose, 55 g/l sorbitol, 250 mg/l cefotaxime, 250 mg/l carbenicillin, 5 g/l Gelrite, pH 5.8).

After incubation under illumination at 28° C. for one week, the callus was divided into 5 portions and plated on nN6CC medium or NBK4CC medium containing 50 mg/l hygromycin and incubated under the same conditions for 10 days. The grown cell aggregates were plated on a regeneration medium (N6salts, N6 vitamins, AA amino acids, 1 g/l casamino acids, 0.5 mg/l kinetin, 20 g/l sucrose, 30 g/l sorbitol, 4 g/l Gelrite, pH 5.8) or (NBK4 majorsalts, B5 minorsalts, B5 vitamins, AA amino acids, 1 g/l casamino acids, 2 mg/l kinetin, 20 g/l maltose, 30 g/l sorbitol, 5 g/l Gelrite, pH 5.8) containing 50 mg/l hygromycin, and incubated under the same conditions for two weeks.

(4) GUS Assay

Cocultured immature embryos and leaf segments excised from regenerated plants were immersed in a 0.1 M phosphate buffer (pH 6.8) containing 0.1% Triton X-100, and allowed to stand at 37° C. for 1 hour. After *Agrobacterium* was removed with the phosphate buffer, a phosphate buffer containing 1.0 mM 5-bromo-4-chloro-3-indolyl-β-D-glucuronic acid (X-gluc) and 20% methanol was added. After treatment at 37° C. for 24 hours, blue-stained tissues were observed under a microscope.

(5) Calculation of Transformation Efficiency

Specifically, calculation of transformation efficiency was performed as follows.

Spots showing transient expression of the GUS gene are found over a wide area of the scutellum in rice immature embryos inoculated with *Agrobacterium*. Spots observed at separate sites on even a single scutellum are thought to be derived from independent transformed cells individually introduced with the gene. When an immature embryo grown after coculture and resting culture was divided into 4 to 6 portions, the callus grown in the presence of hygromycin from 20 to 30 cell clumps obtained by division of even the single immature embryo and the regenerated plants therefrom are thought to be individual transformants.

One hygromycin-resistant callus grown from one cell clump obtained by division was selected and plated on a regeneration medium containing hygromycin. Among the regenerated plants therefrom, those showing the expression of the GUS gene were counted as transformants, and the total number was divided by the number of inoculated immature embryos to calculate the transformation efficiency.

(6) Effects of Pressurization Force on Gene Transduction Efficiency

Collected immature embryos of Koshihikari were placed in a syringe containing the liquid medium, and pressurized at 0 (normal pressure), 0.6, 1.4, 3.2, or 6.6 atm for 15 minutes and then immersed in the *Agrobacterium* suspension. After incubation on the coculture medium for one week, the transient expression of the GUS gene was assayed. Some of control immature embryos treated at normal pressure showed blue staining in about a half of the scutellum, but many of them showed spot expression on the surface of the scutellum. Immature embryos pressurized at 0.6 atm showed a similar type of expression to that of control immature embryos. In contrast, nearly half of immature embryos pressurized at 1.4 atm were blue-stained in about a half of the scutellum. In addition, most of immature embryos pressurized at 3.2 and 6.6 atm were blue-stained on the whole surface of the scutellum, showing that gene transduction efficiency was remarkably improved.

(7) Effects of Pressurization Period on Gene Transduction Efficiency

Collected immature embryos of Koshihikari were placed in a syringe containing the liquid medium, and pressurized at +6.6 atm for 0, 1, 3, 5 or 60 seconds and then immersed in the *Agrobacterium* suspension. After incubation on the coculture medium for one week, the transient expression of the GUS gene was assayed. Control immature embryos treated for 0 second (at normal pressure) showed spot expression on the surface of the scutellum. In contrast, most of immature embryos pressurized at +6.6 atm for 1 second showed transient gene expression on the whole surface of the scutellum. Immature embryos pressurized for 3 seconds or more showed a similar type of expression to that of immature embryos pressurized for 1 second, showing that even a very short period of pressurization is effective for remarkably improving gene transduction efficiency.

(8) Effects of Pressurization in the Presence or Absence of *Agrobacterium* on Transformation Efficiency Collected immature embryos of Koshihikari were placed in a syringe containing sterilized distilled water, the liquid medium alone or the liquid medium supplemented with 100 μM acetosyringone in which *Agrobacterium* LBA4404 (pSB134) cells were suspended at about $1 \times 10^9$ cfu/ml, and pressurized at +6.6 atm for 15 minutes. Immature embryos pressurized in the *Agrobacterium* suspension were plated on the coculture medium after pressurization. Immature embryos pressurized in sterilized distilled water and the liquid medium were immersed in the *Agrobacterium* suspension after pressurization and then plated on the coculture medium. Immature embryos cocultured for one week were assayed for the transient expression of the GUS gene. Some of unpressurized control immature embryos showed blue staining in about a half of the scutellum, but most of them showed spot expression. In contrast, all of the pressurized immature embryos assayed showed the expression of the GUS gene on the whole surface of the scutellum irrespective of whether they were pressurized in the presence or absence of *Agrobacterium*. No difference was found between immature embryos pressurized in sterilized distilled water and the liquid medium.

Immature embryos pressurized in sterilized distilled water and immature embryos pressurized in the presence of *Agrobacterium* were cultured in a medium containing hygromycin, and transformed plants were selected and regenerated. Twelve immature embryos inoculated with *Agrobacterium* after pressurization in sterilized distilled water gave 63 strains of hygromycin-resistant and GUS-positive transformed plants. The transformation efficiency was 525%. On the other hand, 12 immature embryos pressurized in the *Agrobacterium* suspension gave 54 strains of transformed plants with an efficiency of 450%.

The fact that the transformation efficiency was higher after pressurization in the absence of *Agrobacterium* than in the presence of *Agrobacterium* demonstrated that the effect of pressurization on improving gene transduction efficiency as shown herein does not result from the pressurization-promoted infiltration of *Agrobacterium* into plant tissues. In other words, it was shown that the present invention increases gene transduction efficiency via a quite different mechanism from that of Teasdale et al. (WO 99/48335).

(9) Effects of Pressurization in a Gas on Gene Transduction Efficiency

Collected immature embryos of Yukihikari were placed in a syringe containing sterilized distilled water or no liquid. The syringe containing no liquid was pressurized at +5.7 atm for 5 minutes. The syringe containing sterilized distilled water was pressurized at +6.6 atm for 5 minutes. Pressurized immature embryos were returned to normal pressure, and then immersed in the *Agrobacterium* suspension and plated on the coculture medium. Control immature embryos were allowed to stand in sterilized water at normal pressure for 5 minutes, and then immersed in the *Agrobacterium* suspension and plated on the coculture medium. The transient expression of the GUS gene on the scutella of immature embryos cocultured for one week was evaluated on a scale of five ratings from 1 (occasional spot expression) to 5 (expression on the whole surface of the scutellum). Immature embryos pressurized in a gas showed a slightly lower expression level than immature embryos pressurized in distilled water, but clearly showed a wide range of expression as compared with untreated control immature embryos (FIG. 1).

Thus, it was shown that the effect of pressurization on improving gene transduction efficiency is seen when plant tissues are pressurized not only in a liquid but also in a gas before inoculation with *Agrobacterium*.

(10) Effects of Pressurization on Transformation Efficiency

Collected immature embryos (varieties: Koshihikari and Asanohikari) were placed in a syringe containing the liquid medium, and pressurized at +6.6 atm for 15 minutes and then immersed in the *Agrobacterium* suspension. After incubation on the coculture medium for one week, the immature embryos were incubated on a medium containing hygromycin, and transformed plants were selected and regenerated. Leaves of regenerated hygromycin-resistant plants were partially excised and assayed for GUS. The results are shown in Table 1.

TABLE 1

Effects of pressurization on transformation efficiency
(rice, varieties: Koshihikari and Asanohikari)

| Variety | Experiment | Treatment | Number of inoculated immature embryos (A) | Number of HmR, GUS+ plants (B) | Transformation efficiency (B/A) (%) |
|---|---|---|---|---|---|
| Koshihikari | I | No | 12 | 7 | 58.3 |
|  |  | Pressurization | 12 | 66 | 550.0 |
| Koshihikari | II | No | 12 | 17 | 141.7 |
|  |  | Pressurization | 12 | 60 | 500.0 |
| Koshihikari | III | No | 12 | 13 | 108.3 |
|  |  | Pressurization | 12 | 42 | 350.0 |
| Asanohikari | I | No | 12 | 40 | 333.3 |
|  |  | Pressurization | 12 | 119 | 991.7 |

HmR, GUS+: hygromycin-resistant, GUS-positive

Pressurized immature embryos showed transformation efficiencies 3-fold to 9-fold higher or more than those of untreated immature embryos, demonstrating that pressurization is very effective for improving transformation efficiency.

Example 2

Effects of Pressurization on Maize Transformation

Maize immature embryos (variety: A188) having a size of about 1.2 mm were aseptically collected and immersed in a liquid medium for suspending *Agrobacterium* (LS-inf, Ishida et al. 1996). Pressurization was performed by placing immature embryos in a syringe containing the liquid medium and tightening the clamp holding the syringe. Pressurization was performed at +6.6 atm for 5 minutes or +3.2 atm for 10 minutes. Centrifugation was performed by placing immature embryos in an Eppendorf tube containing the liquid medium in a centrifuge at 15,000 rpm, 4° C. for 10 minutes. Pressurized or centrifuged immature embryos were immersed in LS-inf medium supplemented with 100 µM acetosyringone in which *Agrobacterium tumefaciens* LBA4404 (pSB131) strain (Ishida et al. 1996) was suspended at about $1\times10^9$ cfu/ml, and then plated on LS-AS coculture medium. The cocultures were incubated at 25° C. in darkness for 3 days and then assayed for GUS. Control immature embryos were immersed in the liquid medium after collection, and then inoculated with *Agrobacterium* in the same manner.

Figure 2:
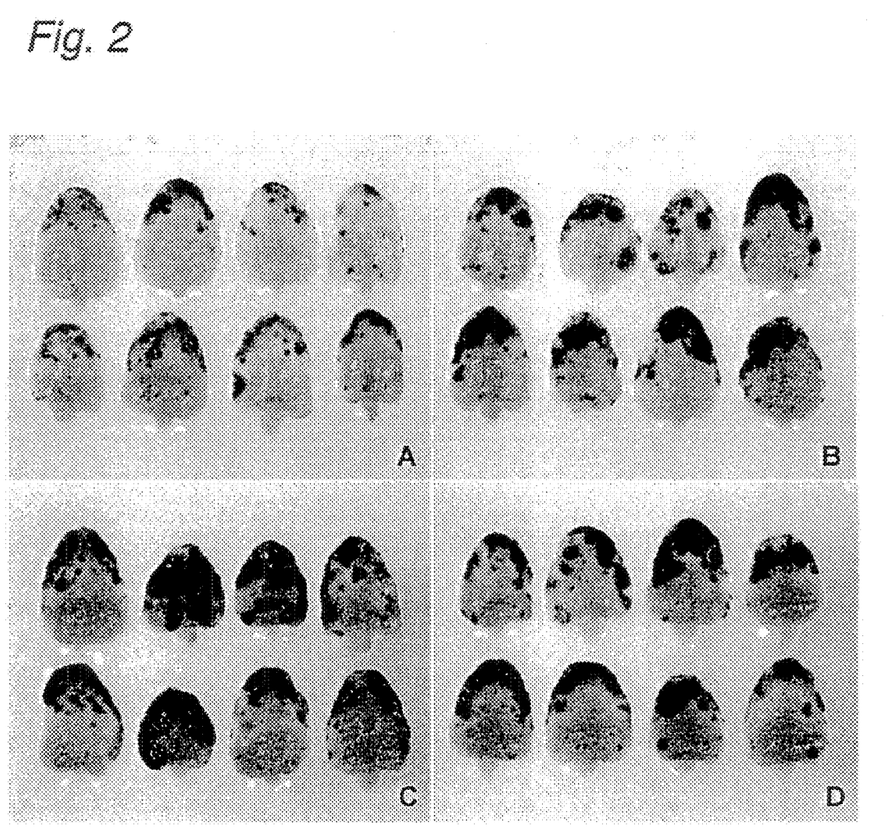
FIGS. 2A-2D show the effects of pressurization on gene transduction (in maize).
A: without pretreatment (control),
B: centrifugation at 15,000 rpm for 10 minutes,
C: pressurization at +3.2 atm for 10 minutes,
D: pressurization at +6.6 atm for 5 minutes.

The control immature embryos showed transient expression of the GUS gene as blue spots on the surface of the scutellum. Immature embryos inoculated with *Agrobacterium* after pressurization or centrifugation showed a real expression such as overall blue staining in about ⅓ of the scutellum. Especially, multiple immature embryos pressurized at +3.2 atm for 10 minutes showed expression of the GUS gene on the whole surface of the scutellum (FIG. 2). It has been already reported that transformation efficiency is increased by centrifuging plant tissues before inoculation with *Agrobacterium* (Hiei et al., WO02/12520).

These facts show that pressurization is effective for improving gene transduction efficiency in not only rice but also another monocotyledon maize and that the effect is comparable to or higher than the effect of centrifugation previously reported.

Example 3

Effects of Pressurization on Tobacco Transformation

Developed leaves of tobacco (variety: Petit Havana SR1) were sterilized by a standard method and then cut into leaf segments of about 1 cm square. Control leaf segments were immersed in LS-R medium (Komari, 1990) in which *Agro-* bacterium tumefaciens LBA4404 (pSB134) was suspended, and gently shaken at 25° C. for 15 minutes, and then immersed in LS-R medium and cultured at 25° C. in darkness for 4 days. Leaf segments in pressurization group were pressurized at +6.6 atm for 15 minutes in a syringe containing LS-R medium and then inoculated with *Agrobacterium* and cultured in the same manner as for the control leaf segments. The cocultured leaf segments were assayed for GUS.

On the basis of the size of the GUS gene expression site shown by each leaf segment after the GUS assay, evaluation was made on a scale of four ratings from 0 (no expression) to 3 (expression on the whole leaf segment). The results are shown in FIG. 3. Control leaf segments often showed GUS expression at the cut section of the leaf, but scarcely showed the expression in a wide area including the inside of the cut section. In contrast, most of leaf segments inoculated with *Agrobacterium* after pressurization showed intense blue staining in a wide area including the cut section and the inside, demonstrating that gene transduction has been achieved in a wide area. This shows that pressurization is effective for increasing gene transduction efficiency in not only monocotyledons such as rice and maize but also dicotyledons Example 4

Effects of Pressurization on Callus Growth

Collected immature embryos of Koshihikari were pressurized at +6.6 atm for 15 minutes in a liquid medium for suspending *Agrobacterium*, and then plated on NBK4CC medium. Control immature embryos were immersed in the same liquid medium at normal pressure, and then plated on NBK4CC medium. After incubation in darkness at 25° C. for one week, 10 immature embryos were measured for fresh weight. Experiments were repeated five times. Both groups were not inoculated with *Agrobacterium*. The results are shown in Table 2.

TABLE 2

Effects of pressurization on cell growth (rice, variety: Koshihikari)

| Treatment | Fresh weight of immature embryos (mg/10 immature embryos) | | | | | Average ± SD |
| --- | --- | --- | --- | --- | --- | --- |
| | Rep. 1 | Rep. 2 | Rep. 3 | Rep. 4 | Rep. 5 | |
| No | 69.2 | 68.5 | 63.6 | 71.5 | 58.5 | 66.3 ± 2.3 |
| Pressurization | 73.1 | 74.0 | 77.2 | 73.2 | 78.1 | 75.1 ± 1.1 |

The fresh weights of immature embryos cultured for 1 week after pressurization were assessed.
Not inoculated with *Agrobacterium*.

The average fresh weight of control immature embryos cultured for one week was 66.3 mg/10 immature embryos. The average fresh weight of immature embryos cultured for the same period after pressurization was 75.1 mg/10 immature embryos, showing a significant difference. The control immature embryos cultured for 1 week appeared pale yellowish white because scutellum surfaces somewhat formed callus. In contrast, pressurized immature embryos appeared thicker yellowish white than the control because of knot-like callus formation. More active growth was also found in pressurized immature embryos by naked eye observation. Thus, it was shown that pressurization is effective for not only improving gene transduction efficiency but also activating cell growth.

The improvement in the cell growth rate of plant tissues by short-term treatment at high pressure among other benefits of the present invention is thought to be based on a different mechanism from that of the method of U.S. Pat. No. 6,492,174 in which the frequency of embryogenic callus formation is increased by incubation at such a low pressure as +0.5 atm for 1-10 weeks, because both methods differ in not only treatment conditions but also the resulting effects.

The invention claimed is:

1. A method of introducing a gene into a plant material via *Agrobacterium*, comprising:
   1) pressurizing the plant material by any one of the following means: i) combining syringes containing plant material, holding the syringes by a clamp and tightening the clamp; ii) supplying a gas into a vessel containing a plant tissue; or iii) submerging in a liquid a plant tissue contained in a bag sealed against the outside air, and then
   2) infecting the plant material with an *Agrobacterium*,
   wherein the pressurization is performed in the range of 1.7 atmospheres to 10 atmospheres.

2. The method of claim 1 wherein pressurization is performed in the range of 2.4 atmospheres to 8 atmospheres.

3. The method of any one of claim 1 or 2 wherein pressurization is performed for 0.1 second to 4 hours.

4. The method of claim 3 wherein pressurization is performed for 1 second to 30 minutes.

5. The method of claim 1, wherein pressurization is performed in a liquid or gas.

6. The method of claim 1 further comprising: subjecting the plant material to at least one treatment selected from the group consisting of heat treatment, centrifugation and sonication before or during the step 2) of infecting the plant material with an *Agrobacterium*.

7. The method of claim 1, wherein the plant material is a monocotyledon.

8. The method of claim 1, wherein the plant material is rice or maize.

9. The method of claim 1, wherein the plant material is a dicotyledon.

10. The method of claim 1, wherein the plant material is tobacco.

11. The method of claim 1, wherein the plant material is an immature embryo.

12. The method of claim 1, further comprising the following steps, after step 2) of infecting the plant material with an *Agrobacterium:*
   3) selecting a transformant, and
   4) optionally regenerating the selected transformant.

13. The method of claim 1, wherein the gene introduction efficiency is improved as compared with cases wherein the step 1) of pressurization is not conducted.

14. A method for producing a transformed plant, comprising:
   1) pressurizing a plant material by any one of the following means: i) combining syringes containing plant material, holding the syringes by a clamp and tightening the clamp; ii) supplying a gas into a vessel containing a plant tissue; or iii) submerging in a liquid a plant tissue contained in a bag sealed against the outside air,
   2) infecting the plant material with an *Agrobacterium*,
   3) selecting a transformed plant cell, and
   4) regenerating the selected transformant, thereby producing a transformed plant,
   wherein the pressurization is performed in the range of 1.7 atmospheres to 10 atmospheres.

15. A method for producing a transformed plant cell, comprising:
1) pressurizing a plant material by any one of the following means: i) combining syringes containing plant material, holding the syringes by a clamp and tightening the clamp; ii) supplying a gas into a vessel containing a plant tissue; or iii) submerging in a liquid a plant tissue contained in a bag sealed against the outside air,
2) infecting the plant material with an *Agrobacterium*, and
3) selecting a transformed plant cell, thereby producing a transformed plant cell, wherein the pressurization is performed in the range of 1.7 atmospheres to 10 atmospheres.

* * * * *